United States Patent
Fuchigami et al.

(10) Patent No.: US 11,348,677 B2
(45) Date of Patent: May 31, 2022

(54) CONVERSION APPARATUS, CONVERSION METHOD, AND PROGRAM

(71) Applicant: FUJIFILM Corporation, Tokyo (JP)

(72) Inventors: Takuya Fuchigami, Tokyo (JP); Mizuki Takei, Tokyo (JP); Keigo Nakamura, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 485 days.

(21) Appl. No.: 16/284,134

(22) Filed: Feb. 25, 2019

(65) Prior Publication Data

US 2019/0267129 A1 Aug. 29, 2019

(30) Foreign Application Priority Data

Feb. 28, 2018 (JP) .............................. JP2018-035110

(51) Int. Cl.
| | | |
|---|---|---|
| *G16H 30/20* | (2018.01) | |
| *G16H 15/00* | (2018.01) | |
| *G06F 16/54* | (2019.01) | |
| *G06F 16/55* | (2019.01) | |

(52) U.S. Cl.
CPC ............. *G16H 30/20* (2018.01); *G06F 16/54* (2019.01); *G06F 16/55* (2019.01); *G16H 15/00* (2018.01)

(58) Field of Classification Search
CPC ... G16H 30/20; G16H 15/00; G06F 16/54–55
See application file for complete search history.

(56) References Cited

U.S. PATENT DOCUMENTS

| | | | | | |
|---|---|---|---|---|---|
| 5,926,638 | A | * | 7/1999 | Inoue .................. | G06F 11/3664 714/E11.21 |
| 6,233,545 | B1 | * | 5/2001 | Datig ..................... | G06N 3/004 706/62 |
| 6,950,753 | B1 | * | 9/2005 | Rzhetsky ............... | G16H 70/60 702/19 |
| 7,539,619 | B1 | * | 5/2009 | Seligman ................ | G10L 15/30 704/277 |
| 8,837,794 | B2 | * | 9/2014 | Nakamura ............. | A61B 5/416 382/128 |

(Continued)

FOREIGN PATENT DOCUMENTS

| | | |
|---|---|---|
| JP | 2001-126007 A | 5/2001 |
| JP | 2004-154237 A | 6/2004 |

(Continued)

OTHER PUBLICATIONS

Pietro Cerveri, Marco Masseroli, and Francesco Pinciroli; "Java Interface to Human Anatomy Knowledge", published in Proceedings of the 26th Euromicro Conference (Sep. 5-7, 2000), retrieved Jun. 17, 2021 from online IEEE Xplore website. (Year: 2000).*

(Continued)

*Primary Examiner* — Shourjo Dasgupta
(74) *Attorney, Agent, or Firm* — Birch, Stewart, Kolasch & Birch, LLP

(57) ABSTRACT

The conversion apparatus includes a selection section that selects a category of a term used for a report of a medical image; and a conversion section that converts an input term of the report to the term of the category selected by the selection section, with reference to a conversion table in which terms of plural types of the categories are associated with each other.

10 Claims, 5 Drawing Sheets

(56) References Cited

U.S. PATENT DOCUMENTS

| | | | | |
|---|---|---|---|---|
| 9,542,647 | B1* | 1/2017 | Mirhaji | G06F 16/2465 |
| 9,679,197 | B1* | 6/2017 | Sills | G06F 3/017 |
| 10,628,553 | B1* | 4/2020 | Murrish | G06F 16/2365 |
| 10,909,176 | B1* | 2/2021 | Naeymi-Rad | G06F 16/86 |
| 2001/0027406 | A1* | 10/2001 | Araki | G06Q 10/06398 705/7.16 |
| 2002/0019679 | A1* | 2/2002 | Okada | G06Q 10/06 700/111 |
| 2003/0004923 | A1* | 1/2003 | Real | G06F 9/453 |
| 2003/0031355 | A1* | 2/2003 | Nagatsuka | G06T 5/009 382/132 |
| 2004/0002660 | A1* | 1/2004 | Mielekamp | G06T 17/00 600/508 |
| 2004/0138922 | A1* | 7/2004 | Hirose | G16H 10/60 705/2 |
| 2005/0154708 | A1* | 7/2005 | Sun | G06F 16/27 |
| 2005/0182773 | A1* | 8/2005 | Feinsmith | G06Q 30/06 |
| 2007/0127790 | A1* | 6/2007 | Lau | G06F 16/58 382/128 |
| 2007/0127798 | A1* | 6/2007 | Chakraborty | G06F 16/94 382/128 |
| 2007/0130206 | A1* | 6/2007 | Zhou | G16H 10/60 |
| 2007/0282917 | A1* | 12/2007 | Nagano | G06F 16/192 |
| 2008/0059773 | A1* | 3/2008 | Fant | G06F 9/4484 712/220 |
| 2009/0067718 | A1* | 3/2009 | Shingai | G06T 3/0012 382/173 |
| 2010/0189366 | A1* | 7/2010 | Iizuka | G16H 15/00 382/209 |
| 2011/0004464 | A1* | 1/2011 | Martino | G06F 40/279 704/9 |
| 2011/0044524 | A1* | 2/2011 | Wang | G01R 33/563 382/131 |
| 2011/0172987 | A1* | 7/2011 | Kent | G06F 40/58 704/E11.001 |
| 2012/0008864 | A1* | 1/2012 | Kanatsu | G06V 30/412 382/176 |
| 2012/0166219 | A1* | 6/2012 | Mansour | G16H 30/20 705/3 |
| 2012/0246105 | A1* | 9/2012 | James | G16H 40/20 706/47 |
| 2012/0330641 | A1* | 12/2012 | Kalb | G06F 40/56 704/1 |
| 2012/0330642 | A1* | 12/2012 | Kalb | G06F 40/55 704/E11.001 |
| 2013/0046529 | A1* | 2/2013 | Grain | G16H 10/60 704/2 |
| 2014/0371578 | A1* | 12/2014 | Auvray | A61B 6/503 600/424 |
| 2015/0036900 | A1* | 2/2015 | Vik | G06T 7/143 382/128 |
| 2015/0293632 | A1* | 10/2015 | Bullock | G06F 3/0484 345/174 |
| 2015/0324522 | A1* | 11/2015 | Chan | G06F 16/24578 705/3 |
| 2016/0117445 | A1* | 4/2016 | Venkat | G16H 10/60 705/3 |
| 2016/0364862 | A1* | 12/2016 | Reicher | G06K 9/66 |
| 2017/0039776 | A1* | 2/2017 | Endo | G06T 3/0093 |
| 2018/0055483 | A1* | 3/2018 | Hunter | A61B 8/54 |
| 2019/0006049 | A1* | 1/2019 | Wolz | G16H 70/60 |
| 2019/0105008 | A1* | 4/2019 | Dehghan Marvast | A61B 6/507 |

FOREIGN PATENT DOCUMENTS

| | | | |
|---|---|---|---|
| JP | 2007-058628 A | 3/2007 | |
| JP | 2008-079770 A | 4/2008 | |
| JP | 2010-167045 A | 8/2010 | |
| WO | WO-2014037922 A2 * | 3/2014 | G06F 19/325 |

OTHER PUBLICATIONS

"Kaiser Permanente Opens Access to CMT to Support HHS Health IT Goals: Frequently Asked Questions", last reviewed Oct. 15, 2010, retrieved Jun. 22, 2021 from https://www.nlm.nih.gov/research/umls/cmt/cmt_faq.html. (Year: 2010).*

Qing Zeng-Treitler and Others, "Making Texts in Electronic Health Records Comprehensible to Consumers: A Prototype Translator", AMIA 2007 Symposium Proceedings pp. 846-850, retrieved Jun. 22, 2021 from https://www.ncbi.nlm.nih.gov/pmc/articles/PMC2655860/pdf/amia-0846-s2007.pdf. (Year: 2007).*

Hari Nandigam and Maxim Topaz, "Mapping Systematized Nomenclature of Medicine—Clinical Terms to International Classification of Diseases . . . ", Perspectives in Health Information Management (Summer 2016), retrieved Jun. 22, 2021 from https://perspectives.ahima.org/mapping-systematized-nomenclature/. (Year: 2016).*

"UMLS Quick Start Guide", last reviewed Jul. 29, 2016, retrieved Jun. 22, 2021 from https://www.nlm.nih.gov/research/umls/quickstart.html. (Year: 2016).*

"Getting Started with MedDRA", dated Mar. 16, 2017, retrieved Jun. 22, 2017 from https://meddra.org/sites/default/files/training/file/000018_getting_started_with_meddra_webinar.pdf. (Year: 2017).*

S. Trent Rosenbloom and Others, "Interface Terminologies: Facilitating Direct Entry of Clinical Data into Electronic Health Record Systems", J AM Med Inform Assoc. 2006, 13:277-288, retrieved Jun. 22, 2021 from https://www.ncbi.nlm.nih.gov/pmc/articles/PMC1513664/pdf/277.pdf. (Year: 2006).*

3M, "Using a medical data dictionary to comply with vocabulary standards and exchange clinical data", published Jun. 2014, retrieved Jun. 22, 2021 from https://www.snomed.org/SNOMED/media/SNOMED/SNOMED-Vendors/3M-Health-Information-Systems--Inc--ci_hdd_white_paper.pdf?ext=.pdf. (Year: 2014).*

Cedric Bousquet and Others, "Formalizing MedDRA to support semantic reasoning on adverse drug reaction terms", Journal of Biomedical Informatics 49 (2014): 282-291, retrieved Jun. 22, 2021 from https://www.sciencedirect.com/science/article/pii/S1532046414000793. (Year: 2014).*

"Integration of Systems | Biology for Majors II", published online on Jun. 30, 2017, retrieved Jun. 22, 2021 from https://courses.lumenlearning.com/suny-wmopen-biology2/chapter/integration-of-systems/. (Year: 2017).*

"Browsers | MedDRA", published online on Jun. 3, 2013, retrieved Jun. 22, 2021 from https://www.meddra.org/browsers. (Year: 2013).*

"What is a Medical Chart? Records and History", published online on May 6, 2015 at https://www.practicefusion.com/medical-charts, retrieved Oct. 5, 2021 (Year: 2015).*

"Using a Medical Data Dictionary to Comply with Vocabulary Standards and Exchange Clinical Data", published by 3M in Jun. 2014, retrieved Oct. 5, 2021 (Year: 2014).*

Margo Imel and James R. Campbell, "Mapping from a Clinical Terminology to a Classification", made available at AHIMA's 75th Anniversary National Convention and Exhibit Proceedings, Oct. 2003, available online at https://library.ahima.org/doc?oid=61537#.YVsj4MpKhaQ, retrieved Oct. 5, 2021 (Year: 2003).*

Yosemite Project, "Interoperability Roadmap", published online on Oct. 30, 2016 at https://yosemiteproject.org/interoperability-roadmap, retrieved Oct. 5, 2021 (Year: 2016).*

Brian Diaz, "What is Semantic Interoperability?", published Oct. 12, 2016, available at https://www.wolterskluwer.com/en/expert-insights/what-is-semantic-interoperability, retrieved Oct. 5, 2021 (Year: 2016).*

Margaret Rogers, "What is a Domain and is this a useful question?", published online in 2013 at https://journals.openedition.org/asp/3810, retrieved Oct. 5, 2021 (Year: 2013).*

Saman Iftikhar et al., "Semantic Interoperability in E-Health for Improved Healthcare", published online on Apr. 25, 2012 at http://www.intechopen.com/books/semantics-in-action-applications-and-scenarios/semantic-interoperability-in-e-health-services-for-improved-healthcare, retrieved Oct. 5, 2021 (Year: 2012).*

Hyeoun-Ae Park and Nick Hardiker, "Clinical Terminologies: A Solution for Semantic Interoperability", published in Journal of Korean Society of Medical Informatics 15-1, 1-11, in 2009, retrieved Oct. 5, 2021 (Year: 2009).*

(56) References Cited

OTHER PUBLICATIONS

Amy P. Abernathy and Jane L. Wheeler, "True translational research: bridging the three phases of translation through data and behavior", published in TBM 1:26-30, 2011, retrieved Oct. 5, 2021 (Year: 2011).*

Shannon Kempe, "Semantic Interoperability: The Future of Healthcare Data", published online on Sep. 16, 2014 at https://www.dataversity.net/semantic-interoperability-future-healthcare-data, retrieved Oct. 5, 2021 (Year: 2014).*

Pamela Faber and Pilar Leon-Arauz, "Specialized Knowledge Representation and the Parameterization of Context", published in Frontiers in Psychology, 7, 196 on Feb. 23, 2016, retrieved Oct. 5, 2021 (Year: 2016).*

Lee Min Lau, Shaun Shakib, "Towards Data Interoperability: Practical Issues in Terminology Implementation and Mapping", presented at the 2005 Health Informatics Conference, Melbourne, Australia, Jul. 31-Aug. 2, 2005, available at https://library.ahima.org/doc?oid=59324#.YVyQe8pKhaQ, retrieved Oct. 5, 2021 (Year: 2005).*

Mihail Bota and Larry W. Swanson, "Collating and curating neuroanatomical nomenclatures: principles and use of the Brain Architecture Knowledge Management System (BAMS)", published Mar. 29, 2010 in Frontiers in Neuroinformatics, retrieved Jan. 27, 2022 (Year: 2010).*

O. Paul Gobee, Daniel Jansma, Marco C. Deruiter, "AnatomicalTerms.info: Heading for an Online Solution to the Anatomical Synonym Problem: Hurdles in Data-reuse from . . . " Clinical Anatomy 24:817-830 (2011), retrieved Jan. 27, 2022 (Year: 2011).*

Japanese Notice of Reasons for Refusal for Japanese Application No. 2018-035110, dated Nov. 17, 2020, with an English translation.

Japanese Office Action for Japanese Application No. 2018-035110, dated Jun. 1, 2021, with English translation.

\* cited by examiner

| VASCULAR TERRITORY (FIRST CATEGORY) | CEREBRAL LOBE (SECOND CATEGORY) |
|---|---|
| ANTERIOR CEREBRAL ARTERY REGION (ACA) | FRONTAL LOBE OR PARIETAL LOBE |
| MIDDLE CEREBRAL ARTERY REGION (MCA) | TEMPORAL LOBE, FRONTAL LOBE OR PARIETAL LOBE |
| POSTERIOR CEREBRAL ARTERY REGION (PCA) | OCCIPITAL LOBE OR BRAIN STEM |
| ... | ... |

| MEDICAL IMAGE | REPORT |
|---|---|
|  | ABNORMALITY IS PRESENT IN LEFT FRONTAL LOBE OR LEFT PARIETAL LOBE |

| MEDICAL IMAGE | REPORT |
|---|---|
|  | ABNORMALITY IS PRESENT IN LEFT FRONTAL LOBE<br><br>WE RECOMMEND "VASCULAR TERRITORY" AS TERM CATEGORY. |

CONVERSION APPARATUS, CONVERSION METHOD, AND PROGRAM

CROSS-REFERENCE TO RELATED APPLICATION

This application claims priority from Japanese Patent Application No. 2018-035110, filed on Feb. 28, 2018, the disclosure of which is incorporated by reference herein in its entirety.

BACKGROUND

Field of the Invention

The present invention relates to a conversion apparatus, a conversion method, and a storage medium storing a program.

Related Art

In the related art, a report creation support system that supports creation of a report relating to a review result of a medical examination has been proposed (see JP2001-126007A). In the report creation support system, information necessary for creation of the report may be input by selectively using a plurality of types of input formats.

Further, an image reading support apparatus that detects an aneurysm candidate detected from a head image, calculates a feature amount of the detected aneurysm candidate, and generates a template sentence of an image reading report using the calculated feature amount has been proposed (see JP2008-079770A).

In addition, a medical information processing apparatus that compares, in a case where it is determined that medical information including predetermined information that is the same type of information as predetermined information included in input medical information is stored in a storage section, priorities of the input predetermined information and the same type of predetermined information, and determines which priority is higher has been proposed (see JP2007-058628A). In the medical information processing apparatus, in a case where it is determined that the priority of the input predetermined information is higher than the other one, the input medical information is stored in the storage section.

However, with respect to a report of a medical image, for example, there is a case where a radiologist who reads a medical image and inputs an image reading result as a report and a doctor who gives a medical examination result to a patient while referring to the report are different from each other. In this case, there is a case where an input term category of a report is not a category suitable for the doctor who refers to the report. That is, in this case, there is a problem that it is not possible to perform an appropriate diagnosis support. This problem may also occur in a case where the doctor refers to previously created reports. However, in the techniques disclosed in JP2001-126007A, JP2008-79770A, and JP2007-58628A, such a problem is not considered.

SUMMARY

In consideration of the above-mentioned problem, an object of the present disclosure is to provide a conversion apparatus, a conversion method, and a storage medium storing a program capable of performing an appropriate diagnosis support.

According to an aspect of the present disclosure, there is provided a conversion apparatus comprising: a selection section that selects a category of a term used for a report of a medical image; and a conversion section that converts an input term of the report to the term of the category selected by the selection section, with reference to association information in which terms of a plurality of types of the categories are associated with each other.

The conversion apparatus according to this aspect of the present disclosure may further comprise: a display controller that performs a control for displaying a region of standard human body data corresponding to the term acquired through the conversion in the conversion section on a display device to be visually recognizable.

The conversion apparatus according to this aspect of the present disclosure may further comprise: a display controller that performs a control for displaying a region on an image that is a target of the report corresponding to the term acquired through the conversion in the conversion section on a display device to be visually recognizable.

In the conversion apparatus according to this aspect of the present disclosure, an organ that is a target of the report may be a brain, and the plurality of types of the categories may include a vascular territory and an anatomical region.

In the conversion apparatus according to this aspect of the present disclosure, an organ that is a target of the report may be a brain, and the plurality of types of the categories include a plurality of types of anatomical regions.

In the conversion apparatus according to this aspect of the present disclosure, an organ that is a target of the report may be a lung, and the plurality of types of the categories include two or more of an anatomical region, a muscular region, a bone region, a respiratory region, and a vascular territory.

In the conversion apparatus according to this aspect of the present disclosure, an organ that is a target of the report may be a lung, and the plurality of types of the categories include a plurality of types of anatomical regions.

The conversion apparatus according to this aspect of the present disclosure may further comprise: a presentation section that presents a candidate of a category suitable for a type of the medical image.

According to another aspect of the present disclosure, there is provided a conversion method executed by a computer, the method comprising: selecting a category of a term used for a report of a medical image; and converting an input term of the report to the term of the selected category, with reference to association information in which terms of a plurality of types of the categories are associated with each other.

According to still another aspect of the present disclosure, there is provided a non-transitory storage medium storing a program that causes a computer to execute a conversion processing, the conversion processing including: selecting a category of a term used for a report of a medical image; and converting an input term of the report to the term of the selected category, with reference to association information in which terms of a plurality of types of the categories are associated with each other.

According to this disclosure, it is possible to perform an appropriate diagnosis support.

DETAILED DESCRIPTION

Hereinafter, embodiments for realizing the technique of the present disclosure will be described in detail with reference to the accompanying drawings.

Figure 1:
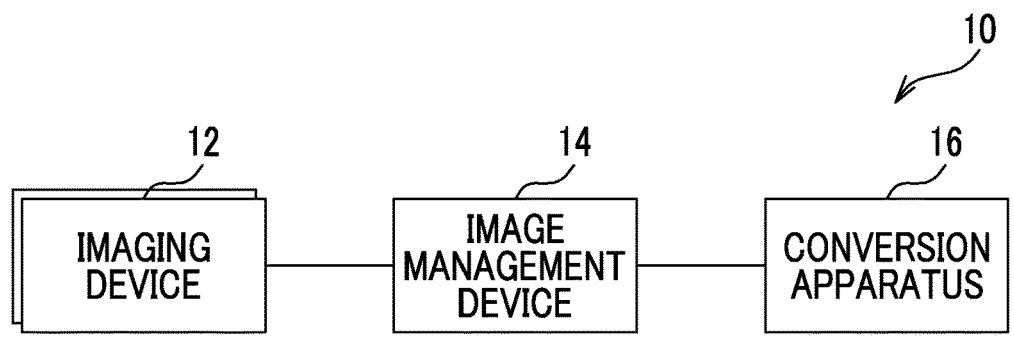
FIG. 1 is a block diagram showing an example of a configuration of a diagnosis system according to an embodiment.

First, a configuration of a diagnosis system 10 according to an embodiment will be described with reference to FIG. 1. As shown in FIG. 1, the diagnosis system 10 includes a plurality of imaging devices 12, an image management device 14, and a conversion apparatus 16. The plurality of imaging devices 12 include an imaging device that captures a computed tomography (CT) image, an imaging device that captures a magnetic resonance imaging (MRI) image, and the like, and are able to capture a plurality of types of medical images.

Each imaging device 12 and the image management device 14 are connected to each other through a network, in which medical image data indicating a medical image obtained through imaging of each imaging device 12 is stored in the image management device 14. Further, the image management device 14 and the conversion apparatus 16 are connected to each other through the network. As an example of the image management device 14, a picture archiving and communication system (PACS) or the like may be used. As an example of the conversion apparatus 16, an information processing apparatus such as a personal computer or a server computer may be used.

Figure 2:
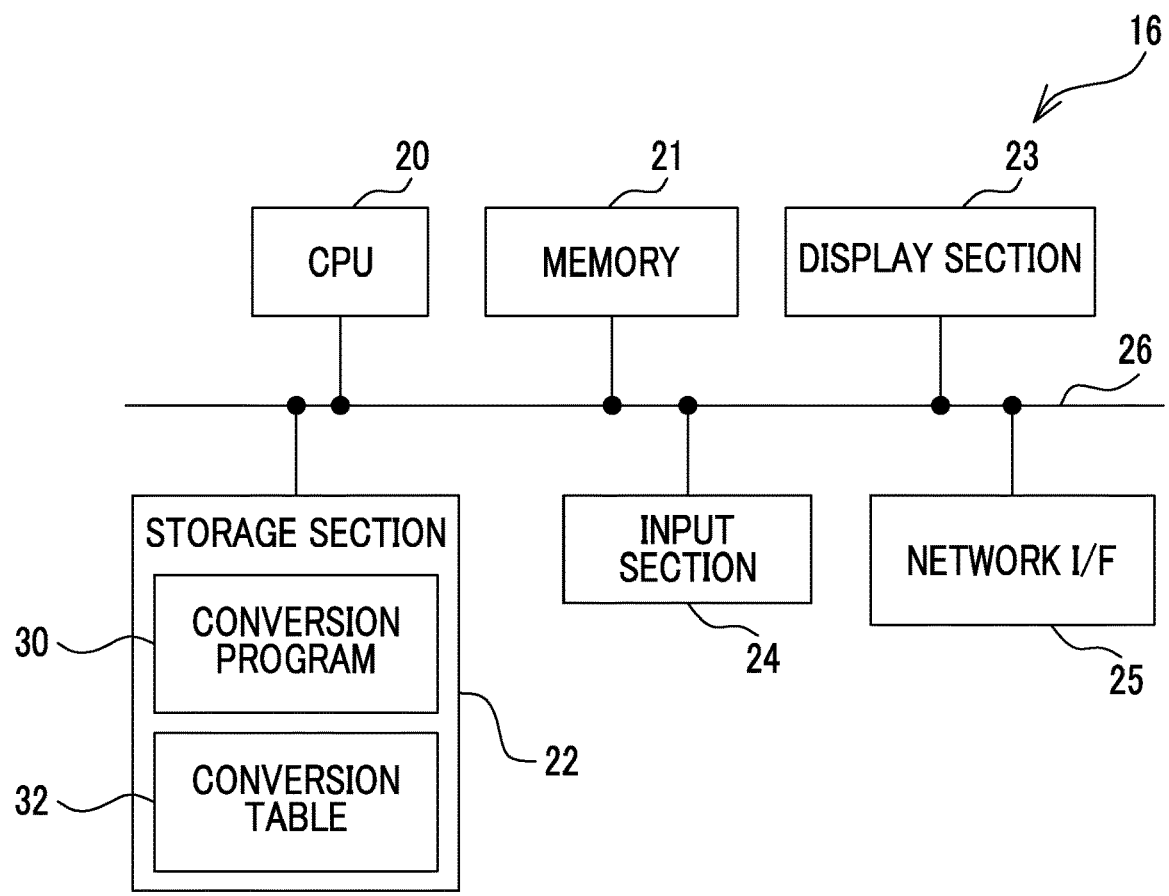
FIG. 2 is a block diagram showing an example of a hardware configuration of a conversion apparatus according to the embodiment.

Then, a hardware configuration of the conversion apparatus 16 according to the embodiment will be descried with reference to FIG. 2. As shown in FIG. 2, the conversion apparatus 16 includes a central processing unit (CPU) 20, a memory 21 that is a temporary storage region, and a non-volatile storage section 22. Further, the conversion apparatus 16 includes a display section 23 such as a liquid crystal display, an input section 24 such as a keyboard or a mouse, and a network interface (I/F) 25 connected to a network. The CPU 20, the memory 21, the storage section 22, the display section 23, the input section 24, and the network I/F 25 are connected to a bus 26.

The storage section 22 is realized by a hard disk drive (HDD), a solid state drive (SSD), a flash memory, or the like. The storage section 22 that is a storage medium stores a conversion program 30. The CPU 20 reads out the conversion program 30 from the storage section 22, expands the read-out conversion program 30 to the memory 21, and executes the expanded conversion program 30.

Figures 3, 4:
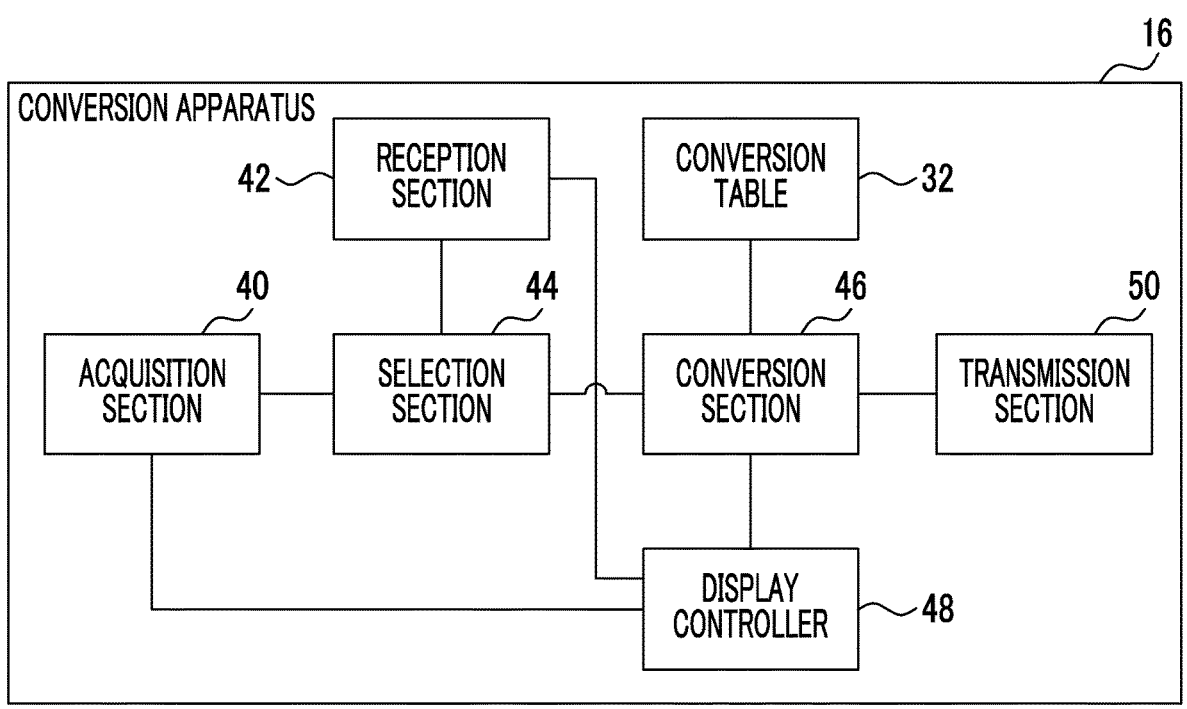
FIG. 3 is a diagram showing an example of a conversion table according to the embodiment.
FIG. 4 is a block diagram showing an example of a functional configuration of the conversion apparatus according to the embodiment.

Further, the storage section 22 stores a conversion table 32. FIG. 3 shows an example of the conversion table 32. As shown in FIG. 3, the conversion table 32 according to this embodiment stores a first category and a second category as term categories used for a report of a medical image, in which the first category and the second category are associated with each other. The conversion table 32 is an example of association information in which terms of a plurality of types of categories are associated with each other. In FIG. 3, an example in which the brain is applied as an organ that is a target of a report of a medical image, a vascular territory is applied as the first category, and a cerebral lobe that is an example of an anatomical region is applied as the second category is shown. As an example of an anatomical region other than the cerebral lobe, regions such as a motor cortex or a motor association cortex, a Broadmann's brain map such as BA4 or BA6, or the like may be used.

Further, in this embodiment, a case where the first category of the conversion table 32 is a conversion source category and the second category is a conversion destination category will be described. In addition, in the conversion table 32 according to this embodiment, a term of the first category and a term of the second category are associated with each other so that an entire region of the brain expressed as the first category is included in the region of the brain expressed as the corresponding second category. Furthermore, the conversion table 32 is stored in the storage section 22 for each of combinations of a plurality of different first categories and second categories.

Next, a functional configuration of the conversion apparatus 16 according to this embodiment will be described with reference to FIG. 4. As shown in FIG. 4, the conversion apparatus 16 includes an acquisition section 40, a reception section 42, a selection section 44, a conversion section 46, a display controller 48, and a transmission section 50. As the CPU 20 executes the conversion program 30, the acquisition section 40, the reception section 42, the selection section 44, the conversion section 46, the display controller 48, and the transmission section 50 performs their functions.

The acquisition section 40 acquires medical image data stored in the image management device 14 and a report corresponding to the medical image data from the image management device 14 through a network.

The reception section 42 receives a conversion command including a category of a term of a conversion destination input through the input section 24 from a user.

The selection section 44 selects the category included in the conversion command received by the reception section 42 as a term category used for a report of a medical image.

The conversion section 46 acquires a term of the second category corresponding to an input term of the report, with reference to the conversion table 32 in which the category to which the input term of the report belongs is the first category and the category selected by the selection section 44 is the second category. Further, the conversion section 46 converts the input term of the report into the acquired term.

The display controller 48 performs a control for displaying a medical image indicated by medical image data acquired by the acquisition section 40 and a report corresponding to the medical image data on the display section 23. Further, in a case where the conversion is performed by the conversion section 46, the display controller 48 performs a control for changing the input term of the report to the term acquired through the conversion in the conversion section 46 to display the result on the display section 23.

Further, in this case, the display controller 48 specifies a position of a region of the brain corresponding to the term acquired through the conversion in the conversion section 46 in standard human body data (so-called a human body atlas). Further, the display controller 48 performs registration using the standard human body data and the medical image (that is, an image that is a target of the report) indicated by the medical image data acquired by the acquisition section 40, with respect to the specified position of the region of the brain in the standard human body data, to derive a position of a region of the brain on the medical image. The display controller 48 performs a control for displaying the region on the medical image corresponding to the term acquired through the conversion in the conversion section 46 to be visually recognizable on the display section 23 in accordance with the derived position.

The transmission section 50 transmits the report of the medical image and the position of the region of the brain on the medical image corresponding to the report to the image management device 14 through the network.

Figure 5:
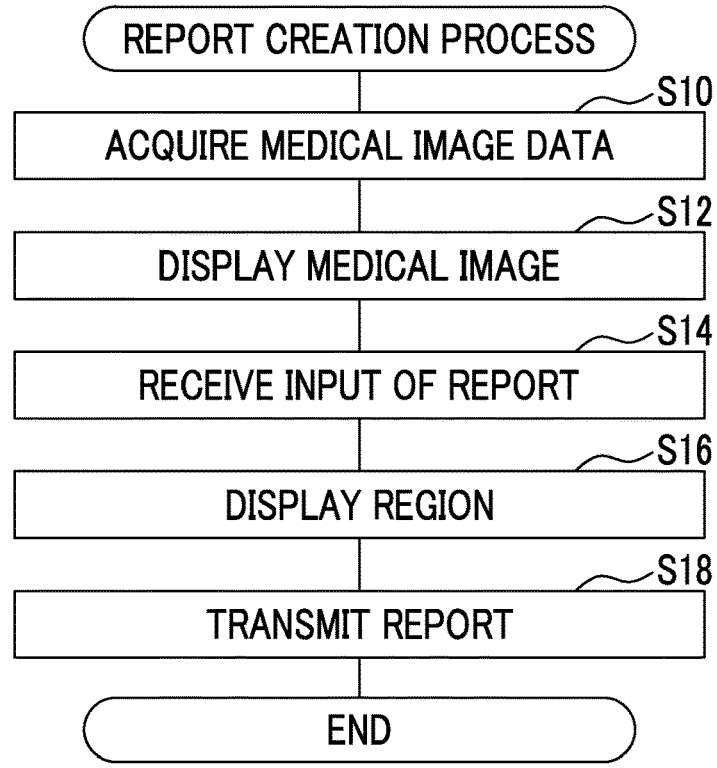
FIG. 5 is a flowchart showing an example of a report creation process according to the embodiment.

Next, an operation of the conversion apparatus 16 according to this embodiment will be described with reference to FIGS. 5 to 8. As the CPU 20 executes the conversion program 30, a report creation process shown in FIG. 5 and a report reference process shown in FIG. 7 are executed. The report creation process shown in FIG. 5 is executed in a case where a report creation command is input through the input section 24 from a user, for example. In this embodiment, the creation command includes identification information of the medical image data that is the target of the report. Further, the report reference process shown in FIG. 7 is executed in a case where a report reference command is input through the input section 24 from the user, for example. In this embodiment, the reference command includes the medical image data that is a reference target and the identification information of the report.

In step S10 shown in FIG. 5, the acquisition section 40 acquires the medical image data corresponding to the identification information included in the report creation command from the image management device 14 through the network. In step S12, the display controller 48 performs a control for displaying the medical image indicated by the medical image data acquired in the process of step S10 on the display section 23. The user inputs the report corresponding to the medical image displayed on the display section 23 through the input section 24.

In step S14, the reception section 42 receives the report input through the input section 24 from the user. In step S16, the display controller 48 specifies a position of a region of the brain corresponding to a term included in the report received in the process of step S14 in the standard human body data. Further, the display controller 48 performs registration using the standard human body data and the medical image indicated by the medical image data acquired in the process of step S10, with respect to the specified position of the region of the brain in the standard human body data, to derive a position of a region of the brain on the medical image.

Figure 6:
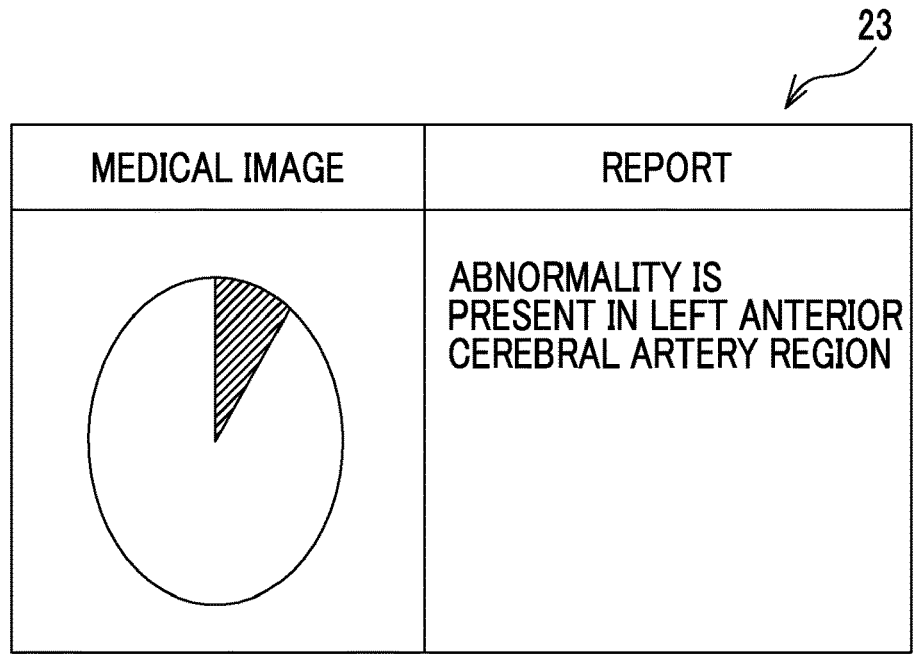
FIG. 6 is a diagram showing an example of a display screen when a report is created according to the embodiment.
Figure 7:
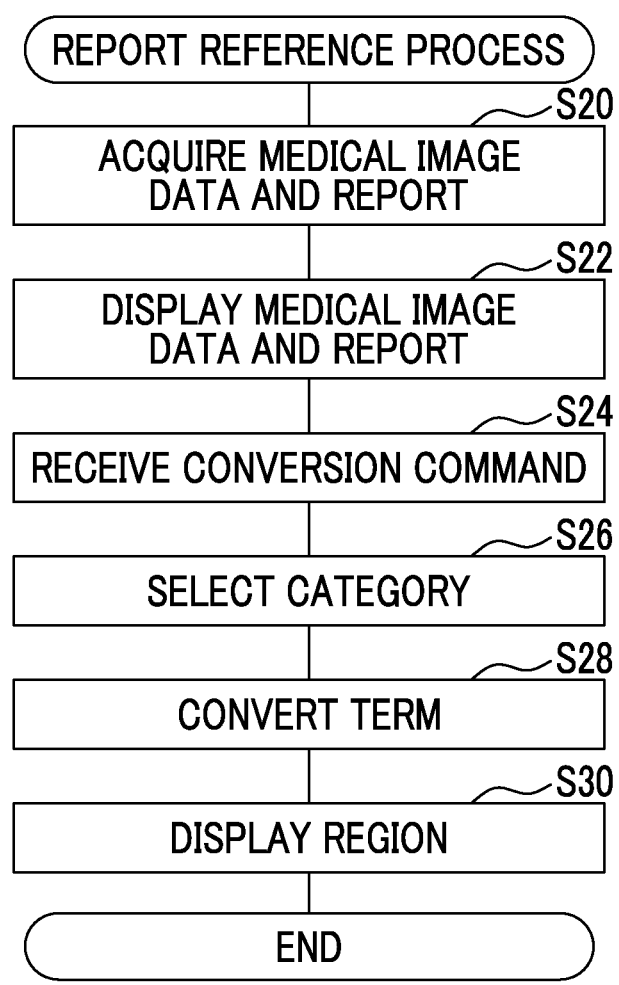
FIG. 7 is a flowchart showing an example of a report reference process according to the embodiment.

Further, as shown in FIG. 6, as one example, the display controller 48 performs a control for displaying the region on the medical image indicated by the medical image data acquired in the process of step S10 to be visually recognizable on the display section 23, in accordance with the derived position. As shown in FIG. 6, in this embodiment, the region of the brain on the medical image corresponding to the term included in the report is displayed on the display section 23 to be superimposed on the medical image in a shaded state.

In step S18, the transmission section 50 transmits the report received in the process of step S14 and the position of the region of the brain corresponding to the term included in the report, specified in the process of step S16, to the image management device 14 through the network. The image management device 14 stores the report and the position of the region of the brain transmitted from the conversion apparatus 16, in association with the medical image data that is the target of the report. The report stored in the image management device 14 is referenced in the report reference process shown in FIG. 7. In a case where the process of step S18 is terminated, the report creation process is terminated.

In step S20 shown in FIG. 7, the acquisition section 40 acquires the medical image data and the report corresponding to the identification information included in the report reference command from the image management device 14 through the network. In step S22, the display controller 48 performs a control for displaying the medical image indicated by the medical image data and the report acquired in the process of step S20 on the display section 23. Through the process of step S22, for example, a screen shown in FIG. 6 is displayed on the display section 23.

In a case where the user wants to convert the category of the term included in the report, the user inputs a conversion command including a category of a term of a conversion destination through the input section 24. In step S24, the reception section 42 receives the conversion command including the category of the term of the conversion destination input through the input section 24 from the user. In step S26, the selection section 44 selects the category included in the conversion command received in the process of step S24 as the category of the term used for the report of the medical image.

In step S28, the conversion section 46 acquires a term of the second category corresponding to an input term of the report, with reference to the conversion table 32 in which the category to which the input term of the report belongs is the first category and the category selected in the process of step S26 is the second category. Further, the conversion section 46 converts the input term of the report into the acquired term.

In step S30, the display controller 48 performs a control for changing the input term of the report to the term acquired through the conversion in the process of step S28 to display the result on the display section 23. Further, the display controller 48 specifies a position of a region of the brain corresponding to the term acquired through the conversion in the process of step S28 in standard human body data. In addition, the display controller 48 performs registration using the standard human body data and the medical image indicated by the medical image data acquired in the process of step S20, with respect to the specified position of the region of the brain in the standard human body data, to derive a position of a region of the brain on the medical image. Furthermore, the display controller 48 performs a control for displaying the region on the medical image corresponding to the term acquired through the conversion in the process of step S28 to be visually recognizable on the display section 23 in accordance with the derived position.

Figure 8:
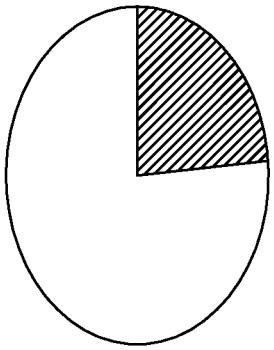
FIG. 8 is a diagram showing an example of a display screen when a report is referred to according to the embodiment.

Through the process of step S30, for example, as shown in FIG. 8, the term of the report is converted, a screen on which the region of the brain is updated in accordance with the term after the conversion is displayed on the display section 23. In a case where the process of step S30 is terminated, the report reference process is terminated.

As described above, according to this embodiment, since a term is converted to a category based on a conversion command from a user, it is possible to perform an appropriate diagnosis support.

In the above-described embodiment, a case where a term of a vascular territory is converted to a term of a cerebral lobe has been described, but the present disclosure is not limited thereto. For example, a configuration in which the term of the vascular territory is converted to a term of a region of the brain or is converted to a term of the Broadmann's brain map may be used. Further, for example, a configuration in which a term of an anatomical region such as a cerebral lobe is converted to a term of a vascular territory may be used. In addition, a configuration in which term conversion is performed between a plurality of types of anatomical regions may be used.

Further, in the above-described embodiment, a case where the brain is applied as an organ that is a target of a report has been described, but the present disclosure is not limited thereto. For example, a configuration in which the lungs are applied as an organ that is a target of a report may be used. In this case, a configuration in which a plurality of types of anatomical regions such as a lung section, a pulmonary lobe, or a pulmonary region may be applied as the first category and the second category may be used. As an example of a term of the lung section, Si (apical segment) or the like may be used, and as an example of a term of the pulmonary lobe, a right upper lobe, a right middle lobe, a right lower lobe, or the like may be used. Further, as an example of a term of the pulmonary region, an upper lung field or the like may be used.

Further, in this case, a configuration which a muscular region, a bone region, a respiratory region, a vascular territory, and the like are applied as the first category and the second category may be used. As an example of a term of the muscular region, an internal intercostal muscle, an external intercostal muscle, or the like may be used. As an example of a term of the bone region, a first rib, a second rib, or the like may be used. Further, as an example of a term of the respiratory region, a central respiratory tract (including main bronchus) or the like may be used. As an example of a term of the vascular territory, a right superior pulmonary vein or the like may be used.

Further, in the above-described embodiment, a case where a region corresponding to a term acquired through conversion in the conversion section 46 is displayed to be visually recognizable on the display section 23, on a medical image that is a target of a report acquired through imaging using the imaging device 12, has been described, but the present disclosure is not limited thereto. A configuration in which a region of standard human body data corresponding to the term acquired through the conversion in the conversion section 46 is displayed to be visually recognizable on the display section 23 may be used. In this case, for example, a configuration in which an image of the brain using the standard human body data is displayed, instead of the image of the brain of the medical image shown in FIG. 6, may be used.

Figure 9:
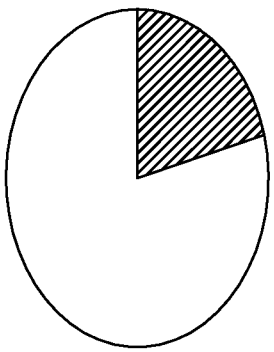
FIG. 9 is a diagram showing an example of a display screen for presenting a category suitable for a type of a medical image according to a modification example.

Further, in the above-described embodiment, a configuration in which candidates of categories of terms suitable for types of medical images are presented may be used. In this case, in a case where an angiographic image such as a CT angiography (CTA) image or an MR angiography (MRA) image is included in a medical image that is a target of a report, for example, as shown in FIG. 9, a configuration in which a message for recommending a vascular territory as a category of a term is displayed on the display section 23 may be used. Further, in this case, a configuration in which an input term of the report is converted into a term of a category suitable for the type of the medical image without presenting the category suitable for the type of the medical image may be used.

Further, in the above-described embodiment, the variety of processes executed as the CPU executes software (program) may be executed by a variety of processors other than the CPU. In this case, as such a processor, a programmable logic device (PLD) of which a circuit configuration after manufacturing is changeable, such as a field programmable gate array (FPGA), a dedicated electric circuit that is a processor having a circuit configuration that is dedicatedly designed for performing a specific process, such as an application specific integrated circuit (ASIC), or the like may be used. In addition, the variety of processes may be executed by one processor among the variety of processors described above, or may be executed by a combination of the same type or different types of two or more processors (for example, a combination of a plurality of FPGAs, a combination of a CPU and an FPGA, or the like). Further, a hardware configuration of the variety of processors is, more specifically, an electric circuit in which circuit elements such as semiconductor elements are combined.

In addition, in the above-described embodiment, a configuration in which the conversion program 30 is stored (installed) in advance in the storage section 22 has been described, but the present disclosure is not limited thereto. A configuration in which the conversion program 30 is provided in the form of being recorded on a storage medium such as a compact disc read only memory (CD-ROM) or a universal serial bus (USB) memory may be used. Further, a configuration in which the conversion program 30 is downloaded from an external device through a network may be used.

Explanation of References

What is claimed is:

1. A conversion apparatus comprising:
a memory; and
a processor coupled to the memory, the processor configured to:
receive selections of terminology to be used for a report of a medical image from a plurality of terminologies; and
convert a term used in the report to a corresponding term of the selected terminology, with reference to association information in which terms of the plurality of terminologies are associated with each other,
wherein the plurality of terminologies include terms for expressing different types of territory classifications of an organ that is a target of the report,
wherein the processor is further configured to:
display, on a display device, the medical image and the report thereof, wherein regions corresponding to the terms used in the report are displayed on the medical image by visual indications; and
based on receiving selection of the terminology and converting the terms, change the indications displayed on the medical image to indications indicating regions corresponding to the converted terms.

2. The conversion apparatus according to claim 1, wherein the processor is further configured to:

perform a control for displaying a region of standard human body data corresponding to the term acquired through the conversion on a display device to be visually recognizable.

3. The conversion apparatus according to claim 1, wherein the processor is further configured to:
perform a control for displaying a region on an image that is a target of the report corresponding to the term acquired through the conversion on a display device to be visually recognizable.

4. The conversion apparatus according to claim 1,
wherein the organ that is the target of the report is a brain, and
wherein the plurality of terminologies include terminologies expressing a vascular territory and an anatomical region.

5. The conversion apparatus according to claim 1,
wherein the organ that is the target of the report is a brain, and
wherein the plurality of terminologies include terminologies expressing a plurality of types of anatomical regions.

6. The conversion apparatus according to claim 1,
wherein the organ that is the target of the report is a lung, and
wherein the plurality of terminologies include terminologies expressing two or more of an anatomical region, a muscular region, a bone region, a respiratory region, and a vascular territory.

7. The conversion apparatus according to claim 1,
wherein the organ that is the target of the report is a lung, and
wherein the plurality of terminologies include terminologies expressing a plurality of types of anatomical regions.

8. The conversion apparatus according to claim 1, wherein the processor is further configured to:
present a candidate of the terminology suitable for a type of the medical image on a display device.

9. A conversion method executed by a computer, the method comprising:
receiving selection of a terminology to be used for a report of a medical image from a plurality of terminologies; and
converting a term used in the report to a corresponding term of the selected terminology, with reference to association information in which terms of the plurality of terminologies are associated with each other,
displaying, on a display device, the medical image and the report thereof, wherein regions corresponding to the terms used in the report are displayed on the medical image by visual indications; and
based on receiving selection of the terminology and converting the terms, changing the indications displayed on the medical image to indications indicating regions corresponding to the converted terms,
wherein the plurality of terminologies includes terms expressing different types of territory classifications of an organ that is a target of the report.

10. A non-transitory storage medium storing a program that causes a computer to execute a conversion processing, the conversion processing comprising:
receiving selection of a terminology to be used for a report of a medical image; and
converting a term used in the report to a corresponding term of the selected terminology, with reference to association information in which terms of the plurality of terminologies are associated with each other,
displaying, on a display device, the medical image and the report thereof, wherein regions corresponding to the terms used in the report are displayed on the medical image by visual indications; and
based on receiving selection of the terminology and converting the terms, changing the indications displayed on the medical image to indications indicating regions corresponding to the converted terms,
wherein the plurality of terminologies includes terms expressing different types of territory classifications of an organ that is a target of the report.

* * * * *